US008598227B2

(12) United States Patent
Palepu

(10) Patent No.: US 8,598,227 B2
(45) Date of Patent: Dec. 3, 2013

(54) EPOPROSTENOL FORMULATION AND METHOD OF MAKING THEREOF

(71) Applicant: Nagesh R. Palepu, Southhampton, PA (US)

(72) Inventor: Nagesh R. Palepu, Southhampton, PA (US)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/621,489

(22) Filed: Sep. 17, 2012

(65) Prior Publication Data

US 2013/0018093 A1 Jan. 17, 2013

Related U.S. Application Data

(62) Division of application No. 12/278,061, filed as application No. PCT/US2007/002948 on Feb. 2, 2007, now Pat. No. 8,318,802.

(60) Provisional application No. 60/764,769, filed on Feb. 3, 2006, provisional application No. 60/772,563, filed on Feb. 13, 2006, provisional application No. 60/783,429, filed on Mar. 20, 2006.

(51) Int. Cl.
*A01N 43/00* (2006.01)
*A01N 43/06* (2006.01)
*A61K 31/33* (2006.01)
*A61K 31/38* (2006.01)

(52) U.S. Cl.
USPC ............................ 514/470; 514/183; 514/444

(58) Field of Classification Search
USPC ......................................... 514/183, 444, 470
See application file for complete search history.

(56) References Cited

U.S. PATENT DOCUMENTS

| 4,335,139 | A | 6/1982 | Watts et al. |
| 6,803,386 | B2 | 10/2004 | Shorr et al. |
| 2002/0177611 | A1 | 11/2002 | McShane et al. |
| 2005/0226893 | A1 | 10/2005 | Juneau et al. |

FOREIGN PATENT DOCUMENTS

EP 0 005 768 12/1979

OTHER PUBLICATIONS

Barst R., et al. *New England Journal of Medicine* vol. 34, Issue 6, pp. 296-301 (1996).
Center for Drug Evaluation and Research, Application No. 22-260, Labeling (Jun. 27, 2008).
Center for Drug Evaluation and Research, Approval Letter to GeneraMedix, Inc. (Jun. 27, 2008).
Cho M.J. and Allen M.A., *Prostaglandins* vol. 15, Issue 6, pp. 943-954 (1978).
Dickinson J. and Murphy R., *Journal of the American Society for Mass Spectrometry* vol. 13, Issue 10, pp. 1227-1234, (2002).
FLOLAN® Prescribing Information, pp. 1-24, GlaxoSmithKline, Research Triangle Park, North Carolina, Sep. 2002.
Japanese Society of Hospital Pharmacists, "Pharmaceutical Interview Form"—Flolan, 3d. Revision; Japanese Standard Commodity Class. No. 87219; (2004) (Translation).
Merck Index, 13th Ed. p. 1408 (2001).
Pre-IND 77,269 (epoprostenol), GeneraMedix (Meeting Minutes) pp. 1-2, Aug. 17, 2007.
Simamora, P. et al., "Effect of pH on Injection Phlebitis", American Chemical Society and C American Pharmaceutical Association, Journal of Pharmaceutical Sciences, vol. 84, No. 4, Apr. 1995, pp. 520-522.
Third Party Observations in European Application No. 07763188.5-2112/1993557 dated Oct. 5, 2012.
Third Party Observations in European Application No. 07763188.5-2112/1993557 dated Oct. 4, 2012.
VELETRI(epoprostenol for injection) Highlights of Prescribing Information, 1995.
Witchey-Lakshmanan, L., et al., "A Novel Formulation of Epoprostenol with Antimicrobial Properties, Administered Under Ambient Conditions, for Treatment of Patients with Pulmonary Arterial Hypertension." *Am.*]. *Respir. Crit Care Med.*, 181, (2009).

*Primary Examiner* — Jeffrey S. Lundgren
*Assistant Examiner* — Chris Simmons
(74) *Attorney, Agent, or Firm* — Hoxie & Associates LLC

(57) ABSTRACT

This invention relates to a stable epoprostenol composition that can be combined with commercially available IV fluids and can be administered in its reconstituted and/or diluted form under ambient conditions of about 15-30° C. for greater than 24 hours. The composition preferably contains (a) epoprostenol or a salt thereof; (b) a alkalinization agent; and (c) a base, such that when reconstituted or in solution, the solution has a pH>11. Methods for making the lyophilized composition are also disclosed.

42 Claims, No Drawings

EPOPROSTENOL FORMULATION AND METHOD OF MAKING THEREOF

This application is a Divisional Application of U.S. Appl. No. 12/278,061, filed on Aug. 1, 2008, which application is a United States National Stage Application under 35 U.S.C. 371 of PCT/US07/02948, filed on Feb. 2, 2007, which claims the benefit of U.S. Provisional Appl. Nos. 60/764,769, filed Feb. 3, 2006; 60/772,563, filed on Feb. 13, 2006; and 60/783,429, filed on Mar. 20, 2006, the contents of each of which are incorporated by reference in their entirety.

FIELD OF THE INVENTION

This invention relates to a stable epoprostenol compositions that can be combined with commercially available IV fluids for parenteral administration under ambient conditions of about 15-30° C. for greater than 24 hours.

BACKGROUND OF INVENTION

Cardiovascular disorders and diseases, and their associated complications are a principal cause of disabilities and deaths of individuals in the United States and Western Europe. For example, in recent years more than 500,000 deaths have occurred annually in the United States alone as a result of coronary artery disease, and an additional 700,000 patients have been hospitalized for myocardial infarction.

There has been an ongoing search for effective long term treatment for disorders and diseases of the heart and arteries, such as atherosclerosis, arteriosclerosis, congestive heart failure, angina pectoris, and other disorders and diseases associated with the cardiovascular system. Prior treatments for such disorders or diseases include administration of vasodilators, angioplasty and by-pass surgery, for example. Such treatments have met with disapproval due to the risks versus the benefits gained by the various treatments. Moreover, such treatments have serious shortcomings in long term effectiveness. The use of vasodilators drugs and mechanical treatments for acute and chronic occlusive vascular diseases of the heart, central, and peripheral vascular system have to date been ineffective for favorable long term results. The outcome with current treatments is minimally impacted because the treatments are directed toward the effects of the underlying disease process rather than the initial molecular cause of the disease or disorder.

For example, the rationale for vasoactive drugs is to reduce blood pressure by acting directly or indirectly on vascular, and/or cardiac, smooth muscle and thereby decreasing vascular resistance and abnormalities to flow. Such drugs do not treat the initial cause of elevated pressure and abnormal flow. Rather, they seek to reduce the resulting effect of the disease or disorder. Such drugs activate the sympathetic nervous system by way of the baroreceptor reflex to produce an increased heart rate and force of myocardial contraction which are not necessarily always beneficial effects. Other side effects from such drugs include headache, heart palpitations, anxiety, mild depression, dry-mouth, unpleasant taste in the mouth, nausea, vomiting, angina, myocardial infarction, congestive heart failure, decreased cardiac output, fluid retention, fatigue, weakness and others. Pharmacological treatment of most diseases is not very specific in its effect on the initial molecular cause of the disease activity, and treats a very limited spectrum of effects in diseases which are multi-factorial.

As a further example, such improved outcome in atherosclerotic vascular diseases is seen with cholesterol reduction and drug treatment for lipid disorders. However, these treatments do not treat the clotting abnormalities associated with these disease states which are known to be the proximate event causing heart attack and stroke. These do not prevent the cellular or molecular reactions attributed to platelets, macrophages, neutrophils, lymphocytes, smooth muscle cells, and other cell types known to be involved in atherosclerosis and complications of the disease.

Likewise, thrombolytic therapy, angioplasty and by-pass surgery have been minimally successful long term. Current mechanical and pharmacological treatments focus on a particular partial or complete occlusion or occluded vessel where, at the particular site, it is either unclogged or by-passed with connecting vessels. These treatments fail to address the physiologic derangements of normally homeostatic systems which allow the occlusive process to begin and progress. Likewise, they fail to address the multi-centric nature of the homeostatic derangements. These failures frequently result in recurrent occlusion in the initially treated vessel, and in microemboli from incomplete resolution of thrombus at the occlusive site treated. No treatment is available for sites judged to be inadequately occluded or stenotic that would respond to currently available, crude technologic methods.

There remains a great need for treatment which prevents the failure of the normal homeostatic controls and which restores these controls once derangements begin to develop. Restoration of the endogenous regulatory systems and cellular domains to a healthy state could prevent the stenosis, occlusion, thrombosis, and thromboembolic processes which occur as a consequence of such derangements. Continuous and episodic restoration of control in the normal molecular processes which finely regulate homeostasis can prevent atherosclerosis, variants thereof, hypertension, congestive heart failure, macro and micro-thrombosis and thromboembolism, and complications of these disease processes, including, but not limited to, myocardial infarction, cerebrovascular accident, related kidney diseases, related central and peripheral nervous system disorders, and related diseases in other cellular systems. In addition, rapid restoration of homeostatic control once injurious processes accelerate and accumulate can minimize both the extent of and duration of consequences on atomic, molecular, membrane, cellular, and organ levels.

Epoprostenol ($PGI_2$, PGX, prostacyclin), a metabolite of arachidonic acid, is a naturally occurring prostaglandin with potent vasodilatory activity and inhibitory activity of platelet aggregation. Epoprostenol is (5Z,9(alpha),11(alpha),13E,15S)-6,9-epoxy-11,15-dihydroxyprosta-5,13-dien-1-oic acid. Epoprostenol sodium has a molecular weight of 374.45 and a molecular formula of $C_{20}H_{31}NaO_5$, and was approved by the U.S. FDA as Flolan (marketed by GlaxoSmithKline) on Sep. 20, 1995, to treat patients with cardio obstructive pulmonary disease.

Flolan for Injection is a sterile sodium salt of epoprostenol formulated for intravenous (IV) administration. Each lyophilized vial of Flolan contains epoprostenol sodium equivalent to 0.5 mg or 1.5 mg epoprostenol, 3.76 mg glycine, 2.93 mg sodium chloride, and 50 mg mannitol. Sodium hydroxide may also be added to adjust pH.

Flolan is a white to off-white powder that must be reconstituted with sterile diluent for Flolan. Sterile diluent for Flolan is supplied in glass vials containing 94 mg glycine, 73.5 mg sodium chloride, sodium hydroxide (added to adjust pH) QS to 50 ml Water for Injection, USP. The reconstituted solution of Flolan has a pH of 10.2 to 10.8 and is increasingly unstable at lower pH.

Epoprostenol sodium (Formula I), an exocyclic vinyl ether, hydrolyzes rapidly, in a pH dependent fashion, to 6-keto-PGF (Formula II). Formula I and Formula II are as follows:

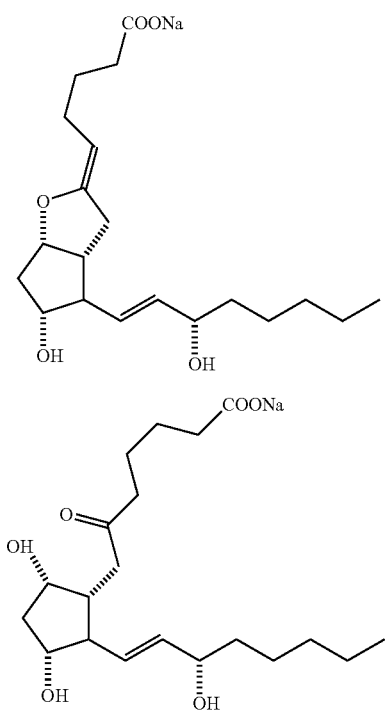

The chemical nature, especially the potential hydrolytic lability, of epoprostenol makes it very difficult to develop a robust formulation. The vinyl ether moiety of $PGI_2$-Na is best stabilized in solution by buffering under basic conditions (>pH 8.8). The half-life, time required for 50% lost in potency, of epoprostenol sodium in water as function of pH is tabulated below in Table 1:

TABLE 1

| Solution stability of Epoprostenol in pH 7.2 to 9.3 | | |
|---|---|---|
| Temperature (C.) | pH | Half-life (hours) |
| 0 | 8.9 | 21.0 |
| 23 | 8.9 | 4.4 |
| 23 | 9.3 | 10.33 |
| 23 | 7.2 | 0.033 |

As shown in the above Table 1, 50% of epoprostenol degrades in about 10 hours at pH 9.3 at 23° C. In order to manufacture a sterile dosage form, the compound should not lose potency for at least 12 hours preferably under ambient conditions. If this is not achievable, the compound must be stable at 4° C. for about 12 hours to process under chilled conditions.

Flolan is supplied as a lyophilized vial with a companion vial which consists 50 ml of a special diluent buffered with glycine and made isotonic with sodium chloride. The pH of the isotonic solution is adjusted to a range of 10.2 to 10.8 with sodium hydroxide. The lyophilized vial is reconstituted with the special diluent and administered to patients suffering from cardiovascular disorders.

Flolan must be reconstituted only with this sterile diluent for Flolan. Reconstituted solutions of Flolan must not be diluted or administered with other parenteral solutions or medications. The reconstituted solutions of Flolan must be protected from light and must be refrigerated at 2° to 8° C. (36° to 46° F.) if not used immediately. The refrigerated solution, however, only lasts two days and must be discarded thereafter. Additionally, the reconstituted solution cannot be frozen, and the solution must be discarded if it is frozen.

Therefore, there remains a need for epoprostenol formulations that can be reconstituted with commercially available IV fluids and do not require refrigeration after reconstitution until use.

SUMMARY OF THE INVENTION

The present inventor has unexpectedly found that epoprostenol solution in the presence of an alkalinizing agent, and high pH (>11) is very stable compared to Flolan. Accordingly, one object of the present invention is to provide pharmaceutical compositions containing epoprostenol or a salt thereof, and at least one alkalinizing agent at pH>11. The composition is characterized by improved stability upon reconstitution with commercially available intravenous (IV) fluids. When reconstituted and/or diluted in commercially available IV fluids, the stability of the present formulation is characterized by at least 90% of the original epoprostenol remaining after 24-48 hours at 15-30° C.

Another object of the present invention is to provide methods for making lyophilized pharmaceutical compositions having epoprostenol and an alkalinizing agent. Such a lyophilized composition when reconstituted has a pH>11.

Yet another object of the present invention is to provide methods for using reconstituted lyophilized pharmaceutical compositions having epoprostenol, and an alkalinizing agent at high pH. The reconstituted solution is preferably used to treat cardiovascular diseases, such as atherosclerosis, arteriosclerosis, congestive heart failure, angina pectoris, cardio obstructive pulmonary disease, and hypertension.

Major advantages of the present invention include hemocompatibility and self-preservation (the ability to pass USP preservative effectiveness test without the presence of preservatives) of the reconstituted and/or diluted solution. Normally, when a chemical is administered intravenously, it should be compatible with blood and should not cause blood cell lysis. Generally, high pH formulations and/or hypotonic solutions cause the lysis of blood cells during the administration. Because the present epoprostenol formulation is administered at high pH (>11), one would expect lysis of the blood cells. However, it was surprisingly found that blood cell lysis did not occur, and that the epoprostenol solution of the present invention showed the same hemocompatibility as normal saline in our studies. Additionally, the reconstituted and/or diluted solution is highly resistant to microorganism and can pass USP preservative effectiveness test.

DETAILED DESCRIPTION OF THE PREFERRED EMBODIMENT

The composition of the present invention contains epoprostenol, or a salt thereof, and an alkalinizing agent. As used henceforth, the term "epoprostenol" refers to either the free acid or a salt of epoprostenol. The ratio of epoprostenol: alkalinizing agent is preferably about 1:25 to about 1:200 by weight, more preferably about 1:25 to 1:100, and most preferably 1:33.3. Most preferred formulations contain either 0.5 mg epoprostenol and 50 mg of arginine, or 1.5 mg of epoprostenol and 50 mg of arginine per vial. The composition preferably also contains sufficient base so that when reconstituted and/or diluted, the pH of the diluted solution is >11.

An alkalinizing agent, as used herein, means an agent that provides alkaline environment (pH>7) when epoprostenol is dissolved in water along with the alkalinizing agent. Additionally, although the alkalinizing agent provides an alkaline environment, it does not contain a basic hydroxide group, but may contain at least one functional group that accepts a proton from water when dissolved in water or water/organic solvents mixture. The alkalinizing agent should have at least one pKa greater than 9.0. Preferably, the alkalinizing agent is in solid phase and is soluble in an aqueous medium. The alkalinizing agents may be, but are not limited to, arginine, lysine, meglumine, N-methyl glucosomine, any other amino acid with a pKa of 9.0 and above, alkaline phosphates such as trisodium phosphates, inorganic carbonates such as sodium carbonates, sodium salts of carboxylic acids such as tetrasodium-EDTA, or combinations thereof. The most preferred alkalinizing agents are arginine and sodium carbonate.

In certain embodiments, the alkalinizing agent may be common buffers including, but not limited to, various salt, acidic, or basic forms of the following anions: citrate, phosphate, tartrate, succinate, adipate, maleate, lactate, acetate, bicarbonate, pyruvate, and carbonate. Representative salts of these buffers which may be used are the sodium and potassium forms, as long as the salt and the amount are physiologically compatible in an injectable composition. Mixtures of these buffering agents may also be used.

The high pH (>11) of the composition (when reconstituted) is preferably achieved by adding an inorganic base. As used herein, an inorganic base is defined as a chemical that contains a free hydroxide ion that can spontaneously accept a proton from water and is used for adjusting the pH of the bulk solution to the target value. The preferred inorganic bases are sodium hydroxide, potassium hydroxide, other alkaline hydroxides, divalent hydroxides such as magnesium hydroxide, and volatile hydroxide such as ammonium hydroxide. Also an organic base, such as primary-, secondary- and tertiary-amines, aromatic amines (such as aniline), and aromatic alcohol (such as phenol) can be used. A combination of both organic and inorganic bases are also appropriate for the present invention. Preferably, the base is added so that the pH of the bulk solution is greater than 11, preferably greater than 12, and, most preferably greater than 13. The preferred base for use with the present invention is sodium hydroxide.

The composition is preferably a lyophile produced by freeze drying (lyophilizing) a bulk solution containing epoprostenol, or a salt thereof, and arginine. The pH of the bulk solution is preferably adjusted to about 12.5-13.5, most preferably 13, by the addition of sodium hydroxide.

The term "lyophilize" with regard to the current pharmaceutical formulations is intended to refer to freeze drying under reduced pressure of a plurality of vials, each containing a unit dose of the epoprostenol formulation of the present invention therein. Lyophilizers, which perform the above described lyophilization, are commercially available and readily operable by those skilled in the art. In one embodiment of the present invention, the bulk solution is lyophilized. A preferred lyophilization process contains three cycles: a freeze cycle, a primary drying cycle, and a secondary drying cycle. The freeze cycle comprises the following steps:

1. Cooling the shelf to about −30° C. or below at the rate of approximately 0.5 to 0.7° C./min. and holding the shelf at this temperature for about 30 to 45 min. or until the product temperature reaches about −25° C. or below
2. Lowering the shelf temperature to about −45° C.±2° C. or below until the product temperature reaches approximately −38±2° C. or less.
3. Holding the product at this temperature for approximately six hours or longer.
4. Applying vacuum until the chamber pressure reaches in the range of 50 milliTorr or less
5. Keeping the shelf temperature at about −45±2° C. for about 45 minutes or more even after vacuum application.

After the freeze cycle, the product is dried in a primary drying cycle, which includes the following steps:

1. Raising the shelf temperature to around 0° C.±2° C. at the heating rate of about 20±2° C./hour, while under vacuum, and continue drying until the product temperature reaches approximately −3±2° C. or higher.
2. Raising the shelf temperature to about 25±2° C. and continue the drying cycle, while under vacuum, continue drying until the product temperature reaches about 20±2° C. or higher.

After the primary drying cycle, the product is further dried under vacuum in a secondary drying cycle by increasing the shelf temperature to approximately 45±2° C. at a rate of about 3±2° C./hr and continue drying till the product reaches about 38±2° C. or higher. Here, preferably, the drying rate is set very slow such that the time taken to reach about 40±2° C. from about 25±2° C. is about 5 hours.

Other pharmaceutically acceptable excipients may also be used in the composition. These excipients may include, but are not limited to, preservatives (present at about 0.1-0.5%), carriers (present at about 1-5%), tonicity modifying agents (sufficient amount to make the solution isotonic), bulking agents (present at about 1-10%), and other conventional components used in formulating pharmaceutical compositions. Preferably, these excipients do not materially affect the fundamental characteristics of the formulation.

Particular preservatives contemplated for use may include benzyl alcohol, parabens, phenol, phenol derivatives, benzalkonium chloride and mixtures thereof. Depending on the particular preservative utilized, the amount of preservative could vary. Preferably the preservative is present at about 0.1-0.5%, most preferably 0.2%.

Representative examples of tonicity modifying agents include sodium chloride, mannitol, dextrose, glucose, lactose and sucrose. The amount of the tonicity modifying agent should be sufficient to render the solution isotonic. This amount varies with the solution and the type of tonicity modifying agent. However, one skilled in the art would be able to determine the amount of tonicity modifying agent to render a particular solution isotonic.

Representative examples of bulking agents include, but are not limited to, hydroxyl ethyl starch (HES); sugars, such as sorbitol, lactose, dextran, maltose, mannose, ribose, sucrose, mannitol, trehalose, lactose, dextran, cyclodextrin; other mono- or polysaccharides; glycine; polyvinylpyrrolidine (PVP); or combinations thereof. The bulking agent may be present at about 1-10%, preferably 1-5%, and most preferably 5%.

In a preferred embodiment, the stable lyophilized formulation contains epoprostenol (or a salt thereof, such as epoprostenol sodium), mannitol, and arginine. The ratio of epoprostenol:arginine is about 1:25 to about 1:200, more preferably about 1:25 to about 1:100, and most preferably about 1:33.3. The ratio of arginine:mannitol is about 5:1 to about 1:5, preferably about 3:1 to about 1:3, and most preferably about 1:1. Preferred formulations contain either 0.5 mg epoprostenol and 50 mg each of arginine and mannitol or 1.5 mg of epoprostenol and 50 mg each of arginine and mannitol per vial. The bulk solution for lyophilization contains either 0.5 mg epoprostenol and 50 mg each of mannitol and arginine, or 1.5 mg of epoprostenol and 50 mg each of arginine and mannitol per ml. The pH of the bulk solution is adjusted to >11 with sodium hydroxide prior to lyophilization.

In another embodiment, the composition of the present composition contains epoprostenol (or a salt thereof, such as epoprostenol sodium), and arginine. The composition may also include a base, which may be an inorganic base, such as sodium hydroxide, or an organic base, or combination of both organic and inorganic base. The base is added so that the pH of the bulk solution is greater than 11, preferably greater than 12, and, most preferably 13 or higher.

In another embodiment, the present invention developed a stable lyophilized formulation containing epoprostenol (or a salt thereof, such as epoprostenol sodium), mannitol, and a base, preferably in a ratio of about 1:25 to about 1:200 (epoprostenol:mannitol), more preferably 1:100 and most preferably 1:33.3. Preferred formulations contain either 0.5 mg epoprostenol and 50 mg of mannitol or 1.5 mg of epoprostenol and 50 mg mannitol per vial. The bulk solution for lyophilization contains either both 0.5 mg epoprostenol and 50 mg of mannitol or 1.5 mg of epoprostenol and 50 mg mannitol per ml. The pH of the bulk solution is adjusted to 13.0 with the base.

The lyophilized composition may be reconstituted using commercially available IV fluids. These fluids include, but are not limited to, water for injection (WFI), including bacteriostatic WFI and sterile WFI; 0.9% sodium chloride solution (normal saline); lactated Ringer's solution; Ringer's solution; sodium carbonate solution; bicarbonate solution; amino acid solution; and similar readily available pharmaceutical diluents. The preferred diluent is normal saline or lactated Ringer's solution. When reconstituted and/or diluted, the pH of the reconstituted solution is greater than about 11, preferably greater than about 11.3, more preferably greater than about 11.5, and most preferably greater than about 11.8.

The pharmaceutical composition of the present invention is formulated in a unit dose or in multi-dose form, and may be in an injectable or infusible form such as solution, suspension, or emulsion. Preferably, it is prepared as dried, lyophilized powder, which can be reconstituted into the liquid solution, suspension, or emulsion before administration by any of various methods including 'IV routes of administration. Preferably, the lyophilized composition is reconstituted to 100-10 µg/ml, preferably 10 µg/ml for administration. This diluted solution is 90% stable (90% of the original epoprostenol remains) at 15-30° C. after 24-48 hrs.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in these examples.

EXAMPLE 1

Stability of Flolan for Injection

In order to understand the stability of a version of epoprostenol currently available on the market (Flolan), we have prepared lyophilized vials of epoprostenol as well as the diluent according to the composition given in the Physician's Desk Reference (PDR). Flolan for Injection is a sterile sodium salt formulated for intravenous (IV) administration. Each lyophilized vial of Flolan contains epoprostenol sodium equivalent to 0.5 mg or 1.5 mg epoprostenol, 3.76 mg glycine, 2.93 mg sodium chloride, and 50 mg mannitol. Sodium hydroxide may have been added to adjust pH. We prepared our Flolan simulated products using this formula.

Flolan must be reconstituted with sterile diluent made specifically for Flolan. Sterile diluent for Flolan is supplied in glass vials containing 94 mg glycine, 73.5 mg sodium chloride, sodium hydroxide (added to adjust pH) QS to 50 ml Water for Injection, USP. The diluent pH range listed in the PDR is 10.2 to 10.8, hence we prepared the diluent as above and adjusted the pH of the diluent to 10.5. Our vials of simulated product were reconstituted with the diluent per the instructions given in the PDR and the stability of the diluent was monitored 5±1° C. The stability data is summarized in the Table 2 below. The PDR also describes that the diluted solution must be administered at <25° C. Since the drug is continuously infused via an infusion pump, the solution pouch is usually kept in an ice pack which needs to be changed every 8 hours.

TABLE 2

Solution stability of Flolan formulation at 5 ± 1° C., pH 10.5

| TIME (HRS) | % Assay of Epoprostenol by Area | Area % of 6-keto PGF et al. impurities |
| --- | --- | --- |
| Initial | 100.0 | 0.21 |
| 2.5 | 99.7 | 0.31 |
| 5.0 | 99.3 | 0.39 |
| 7.5 | 98.9 | 0.44 |
| 10.0 | 98.5 | 0.55 |
| 12.5 | 98.0 | 0.61 |
| 15.0 | 97.5 | 0.71 |
| 18.0 | 97.1 | 0.80 |
| 39.0 | 86.7 | 4.49 |
| 53.0 | 80.3 | 6.59 |
| 77.0 | 61.6 | 12.9 |

As shown in Table 2, the product degrades at a rate of approximately 0.5 to 1% for every three hours in the first 39 hours; therefore, in 24 hours it degrades about 4-8%. Later times show an even faster degradation rate.

We have also conducted the solution stability of the Flolan formulation at 29±1° C. The Flolan formulation degraded just over 4% in 1 hour (presented in Table 3) while a formulation of this present invention lost of just over 2% of drug in 24 hours (presented in Table 7).

TABLE 3

Solution stability of Flolan formulation pH 10.5, at 29 ± 1° C.

| TIME (HRS) | % ASSAY of Epoprostenol by Area | Area % of 6-keto PGF et al. impurities |
| --- | --- | --- |
| Initial | 100.0 | 0.08 |
| 1 | 95.6 | 1.48 |
| 2 | 91.2 | 2.54 |
| 3 | 87.1 | 3.54 |
| 4 | 83.4 | 4.41 |
| 5 | 80.4 | 5.39 |

EXAMPLE 2

Stability of Epoprostenol with Arginine

A solution of epoprostenol and 50 mg/ml of arginine was prepared and the stability of this solution at 5° C. was determined. The resulting data are presented in the Table 4:

TABLE 4

Solution stability of Epoprostenol in presence of 50 mg/ml
of arginine, pH 11.9, at 5 ± 1° C.

| TIME (HRS) | % Assay of Epoprostenol by Area | Area % of 6-keto et al. impurities |
|---|---|---|
| Initial | 100.0 | 0.15 |
| 2 | 99.9 | 0.19 |
| 4 | 99.8 | 0.19 |
| 6 | 99.8 | 0.21 |
| 8 | 99.7 | 0.22 |
| 10 | 99.6 | 0.23 |
| 12.5 | 99.6 | 0.25 |
| 14.5 | 99.6 | 0.26 |
| 39 | 99.5 | 0.63 |
| 53 | 98.6 | 1.15 |
| 77 | 92.7 | 2.05 |
| 100 | 92.5 | 2.10 |
| 124 | 92.5 | 2.25 |

As shown in the Table 4, the composition lost only 1.4% in potency at 53 hours, while the Flolan formulation (Table 2) showed approximately 20% potency loss during this time. The data suggest that epoprostenol solution could be continuously administered for 5 days without changing the solution in the reservoir, assuming sufficient volume and sterility are assured. This is a significant improvement over the Flolan because the Flolan solution in the pump reservoir needs to be replaced every 12 hours.

Stability of the same formulation was also conducted at pH 11.2; and the data are summarized in the Table 5 below:

TABLE 5

Solution stability of Epoprostenol in presence of 50 mg/ml
of arginine, pH 11.2, at 5 ± 1° C.

| TIME (HRS) | % Assay of Epoprostenol by Area | Area % of 6-Keto et al. impurities |
|---|---|---|
| Initial | 100.0 | — |
| 4.0 | 99.5 | 0.28 |
| 7.0 | 99.0 | 0.39 |
| 10.0 | 98.6 | 0.53 |
| 11.5 | 98.3 | 0.57 |
| 17.5 | 97.3 | 0.80 |

Even at pH 11.2, the data suggest better stability than the Flolan formulation (Table 2).

EXAMPLE 3

Stability of Reconstituted Lyophile

In the next set of experiments, the pH of the solution containing epoprostenol and arginine was adjusted to 13.0 with sodium hydroxide, and lyophilized. Upon reconstitution of the lyophile with 1 ml of Water for Injection, the reconstituted solution contains 50 mg/ml arginine and 0.5 mg/ml epoprostenol. The pH of the solution is 13.0. The stability data are presented in Table 6 for 5° C. and Table 7 for 29° C. below:

TABLE 6

Solution stability of Epoprostenol in presence of 50
mg/ml arginine at 5 ± 1° C., pH 13.0

| TIME (Hours) | % Assay of Epoprostenol by Area | Area % of 6-keto PGF et al. impurities |
|---|---|---|
| Initial | 100.0 | 0.16 |
| 14.5 | 99.8 | 0.20 |
| 53 | 98.8 | 0.29 |
| 124 | 98.0 | 0.40 |
| 148 | 97.6 | 0.45 |
| 192 | 97.3 | 0.47 |
| 240 | 96.9 | 0.61 |
| 480 | 96.6 | 0.70 |

The current invention therefore shows only 3.4% loss of potency over 480 hours, or 0.007%/hour on average when held at 5° C.

In addition, the advantage with the present invention is that the formulation does not require a special diluent. The lyophilized formulation can be reconstituted with water for injection to a concentration as low as 5 ng/ml and the pH of the solution is still maintained above 11.0 due to buffer capacity of arginine with basic $pK_a$ of 13.2 and 10.8 and the additional base added for the pH adjustment.

TABLE 7

Solution stability of Epoprostenol in presence of 50 mg/ml
of arginine, pH 13.0, at 29 ± 1° C.

| TIME (HRS) | % ASSAY of Epoprostenol by Area | Area % of 6-keto et al. impurities |
|---|---|---|
| Initial | 100.0 | 0.072 |
| 1 | 100.0 | 0.087 |
| 5 | 99.8 | 0.18 |
| 7 | 99.3 | 0.21 |
| 8 | 99.2 | 0.25 |
| 9 | 99.1 | 0.29 |
| 10 | 98.8 | 0.28 |
| 11 | 98.6 | 0.29 |
| 12 | 98.5 | 0.30 |
| 13 | 98.1 | 0.38 |
| 14 | 98.0 | 0.37 |
| 15 | 97.8 | 0.39 |
| 24 | 97.5 | 0.39 |
| 36 | 97.5 | 0.45 |

Finally, because only 1.5% degradation was observed in 12 hours at 29° C., it is conceivable to manufacture this formulation in a parenteral facility without cooling the bulk solution to 5° C. This would not be possible for the currently available product because the pH of the bulk solution is 10.5 and the product would have to be manufactured at 5±1° C. within 12 hours or significant degradation is occurs.

EXAMPLE 4

Comparison of Various Epoprostenol Compositions

In the next stage of development, we screened several lyophilized formulations with the pH of bulk solution for lyophilization adjusted between 10.5 and 13.0 in the presence of different excipients. The composition of the studies formulations are detailed in Table 8 and the stability data are summarized in the Table 9 below.

TABLE 8

Stability of several Epoprostenol prototype formulations

Quantity (mg) of Excipient used in Formulations

| Batch # | EPP | Trehalose | Arginine | Mannitol | HES | NaCl | Glycine | Na2CO3 | Bulk. Sol. pH |
|---|---|---|---|---|---|---|---|---|---|
| EPP-7 | 0.5 | | 50 | | | | | | 13 |
| EPP-8 | 0.5 | | | 50 | | 3 | 3.75 | | 10.5 |
| EPP-10 | 0.5 | | 50 | | 50 | | | | 13 |
| EPP-12 | 0.5 | | | | | | | 100 | 13 |
| EPP-13 | 0.5 | | 50 | | 50 | | | | 13 |
| EPP-14 | 0.5 | | | | 50 | | | | 13 |
| EPP-19 | 0.5 | | | 50 | | | | | 12 |
| EPP-20 | 0.5 | | | 50 | | | | | 13 |
| EPP-23 | 0.5 | | | 50 | 50 | | | | 13 |
| EPP-24 | 0.5 | | | 50 | 50 | | | | 11 |
| EPP-25 | 0.5 | | 50 | 50 | | | | | 12 |
| EPP-26 | 0.5 | | 50 | 50 | | | | | 13 |
| EPP-27 | 0.5 | | 50 | | | | | | 12 |
| EPP-30 | 0.5 | | | 100 | | | 97.76 | | 11 |
| EPP-31 | 0.5 | | | 100 | | | 97.76 | | 12 |
| EPP-32 | 0.5 | 50 | | | | | 97.76 | | 11 |
| EPP-33 | 0.5 | 50 | | | | | | | 12 |
| EPP-38 | 0.5 | | 50 | | | | | | 13 |

EPP: epoprostenol sodium; HES: Hydroxy ethyl starch; Bulk. Sol. pH: bulk solution pH

TABLE 9

Stability of Epoprostenol prototype formulations

Stability (% Initial) stored at 40° C.

| Batch # | 15 Days | 30 Days | 60 Days | 90 Days |
|---|---|---|---|---|
| EPP-7 | 99 | 97 | NP | NP |
| EPP-8 | 40 | 0 | NP | NP |
| EPP-10 | 99 | 99 | 99 | 100 |
| EPP-12 | 76 | NP | NP | NP |
| EPP-13 | 99 | 98 | 99 | 97 |
| EPP-14 | 100 | 96 | 97 | 83 |
| EPP-19(25%)* | 87 | NP | NP | NP |
| EPP-20(40%) | 29 | NP | NP | NP |
| EPP-23 | 94 | | 96 | |
| EPP-24 | 0 | | | |
| EPP-25 | 60 | 35 | 24 | |
| EPP-26(11%) | 100 | 101 | 100 | |
| EPP-27 | 60 | | | |
| EPP-30 | 88 | | | |
| EPP-31 | 90 | 96 | | |
| EPP-32 | 76 | 74 | | |
| EPP-33 | 95 | 100 | | |
| EPP-38(13%) | 94 | | | |

*The numbers in parenthesis denote the water content of the lyophile
NP: Not performed During the lyophilization several batches were lyophilized together resulting in different moisture contents. The moisture contents of selected samples (EPP-19, 20. 26, and 38) were also measured. As shown in the Table 8 above, the stability of epoprostenol is better at pH 13 compared to lower pH samples. Formulations containing mannitol/HES or mannitol/arginine or HES/sodium carbonate showed excellent stability.

In the next step, formulations containing arginine/mannitol, with the pH of bulk solution adjusted to 13, were selected for lyophilization. Since moisture content varies from batch to batch, the lyophilization cycle was optimized to consistently produce moisture contents less than 12%, using the three cycle lyophilization process discussed above. Using the optimized lyophilization process, the following formulations were manufactured:

1. Three batches of epoprostenol (0.5 mg)/arginine (50 mg)/mannitol (50 mg)/pH 13 per vial
2. One batch of epoprostenol (0.5 mg)/arginine (50 mg)/mannitol (50 mg)/pH 12 per vial
3. Two batches of epoprostenol (0.5 mg)/arginine (50 mg)/trehalose (50 mg)/pH 13 per vial
4. One batch of epoprostenol (0.5 mg)/arginine (50 mg)/trehalose (50 mg)/pH 12 per vial
5. One batch each of the Flolan composition adjusted to pH 12 and 13.

The moisture content of each of these batches ranged between between 7-10%.

Three-month solid state stability data for the selected formulations are presented in the Tables 10-18 below:

TABLE 10

Batch # EX-01: EPP/mannitol/Arginine/pH::0.5/50/50/13*

| Storage Temp | Assay Time | EPP mg/vial | % of EPP | 6-PGF mg/vial | % of 6-PGF | Additional Peaks Area % |
|---|---|---|---|---|---|---|
| 40° C. | Initial | 0.49 | 100 | Nil | Nil | NA |
| | 15 days | 0.49 | 100 | Nil | Nil | NA |
| | 1 month | 0.50 | 102 | Nil | Nil | 0.2 |
| | 2 months | 0.48 | 98 | 0.003 | 0.65 | 0.72 |
| | 3 months | 0.48 | 98 | 0.002 | 0.49 | 0.78 |
| 25° C. | 3 months | 0.48 | 98 | 0.00034 | 0.07 | 0.12 |

*EPP/mannitol/arginine/pH::0.5/50/50/13 = 0.5 mg/vial epoprostenol, 50 mg/vial mannitol, 50 mg/vial arginine, and pH 13.

TABLE 11

Batch # EX-02: EPP/mannitol/Arginine/pH::0.5/50/50/13

| Storage Temp | Assay Time | EPP mg/vial | % of EPP | 6-PGF mg/vial | % of 6-PGF | Additional Peaks Area % |
|---|---|---|---|---|---|---|
| 40° C. | Initial | 0.49 | 100 | Nil | Nil | NA |
| | 15 days | 0.49 | 100 | Nil | Nil | NA |
| | 1 month | 0.50 | 102 | Nil | Nil | 0.2 |
| | 2 months | 0.48 | 98 | 0.003 | 0.64 | 0.73 |
| | 3 months | 0.49 | 100 | 0.0041 | 0.84 | 0.87 |
| 25° C. | 3 months | 0.49 | 100 | 0.0004 | 0.08 | 0.12 |

TABLE 12

Batch # EX-03: EPP/mannitol/Arginine/pH::0.5/50/50/13

| Storage Temp | Assay Time | EPP mg/vial | % of EPP | 6-PGF mg/vial | % of 6-PGF | Additional Peaks Area % |
|---|---|---|---|---|---|---|
| 40° C. | Initial | 0.49 | 100 | Nil | Nil | NA |
| | 15 days | 0.49 | 100 | Nil | Nil | NA |
| | 1 month | 0.50 | 102 | Nil | Nil | 0.2 |
| | 2 months | 0.50 | 102 | 0.0021 | 0.41 | 0.66 |
| | 3 months | 0.48 | 98 | 0.0041 | 0.84 | 1.07 |
| 25° C. | 3 months | 0.49 | 100 | 0.00044 | 0.09 | 0.12 |

TABLE 13

Batch # EX-07: EPP/mannitol/Arginine/pH::0.5/50/50/12

| Storage Temp | Assay Time | EPP mg/vial | % of EPP | 6-PGF mg/vial | % of 6-keto | Additional Peaks Area % |
|---|---|---|---|---|---|---|
| 40° C. | Initial | 0.47 | 100 | 0.002 | 0.36 | 0.08 |
| | 15 days | 0.013 | 2.8 | 0.07 | 14.8 | 0.76 |
| | 1 month | 0.008 | 1.7 | 0.072 | 15.4 | 0.66 |

TABLE 14

Batch # EX-04: EPP/trehalose/Arginine/pH::0.5/50/50/13

| Storage Temp | Assay Time | EPP mg/vial | % of EPP | 6-PGF mg/vial | % of 6-PGF | Additional Peaks Area % |
|---|---|---|---|---|---|---|
| 40° C. | Initial | 0.52 | 100 | 0.0006 | 0.11 | 0.08 |
| | 15 days | 0.52 | 100 | 0.0007 | 0.13 | 0.08 |
| | 1 month | 0.52 | 100 | NIL | NIL | 0.12 |
| | 2 months | 0.49 | 94 | 0.007 | 1.4 | 0.38 |
| | 3 months | 0.49 | 94 | 0.0114 | 2.2 | 0.80 |
| 25° C. | 3 months | 0.52 | 100 | 0.0006 | 0.12 | 0.17 |

TABLE 15

Batch # EX-06: EPP/Arginine/Trehalose/pH::0.5/50/50/13

| Storage Temp | Assay Time | EPP mg/vial | % of EPP | 6-PGF mg/vial | % of 6-PGF | Additional Peaks Area % |
|---|---|---|---|---|---|---|
| 40° C. | Initial | 0.52 | 100 | 0.0006 | 0.12 | 0.08 |
| | 15 days | 0.52 | 100 | 0.0006 | 0.12 | 0.08 |
| | 1 month | 0.50 | 96 | NIL | NIL | 0.11 |
| | 2 months | 0.48 | 92 | 0.011 | 2.08 | 0.31 |
| | 3 months | 0.49 | 94 | 0.012 | 2.3 | 0.87 |
| 25° C. | 3 months | 0.51 | 98 | 0.0001 | 0.02 | 0.17 |

TABLE 16

Batch # EX-05: EPP/trehalose/Arginine/pH::0.5/50/50/12

| Storage Temp | Assay Time | EPP mg/vial | % of EPP | 6-PGF mg/vial | % of EPP | Additional Peaks Area % |
|---|---|---|---|---|---|---|
| 40° C. | Initial | 0.51 | 100.0 | Nil | NIL | 0.15 |
| | 15 days | 0.51 | 100.0 | 0.003 | 0.57 | 0.2 |
| | 1 month | 0.40 | 78 | 0.003 | 0.74 | 0.45 |
| | 2 months | 0.32 | 63 | 0.004 | 0.82 | 1.33 |

TABLE 17

Batch # EX-08: Flolan simulated formulation*: pH 12

| Storage Temp | Assay Time | EPP mg/vial | % of Initial | 6-PGF mg/vial | % of EPP | Additional Peaks Area % |
|---|---|---|---|---|---|---|
| 40° C. | Initial | 0.50 | 100.0 | 0.0014 | 0.28 | 0.11 |
| | 15 days | 0.03 | 6.0 | 0.072 | 14.4 | 1.56 |
| | 1 month | 0.011 | 2.2 | 0.032 | 6.4 | 0.78 |

*Flolan simulation formulation refers to a formulation that is identical to the commercially available Flolan marketed by GlaxoSmithKline, except that the pH has been adjusted to the indicated pH.

TABLE 18

Batch # EX-09: Flolan simulated formulation: pH 13

| Storage Temp | Assay Time | EPP mg/vial | % of EPP | 6-PGF mg/vial | % of 6-PGF | Additional Peaks Area % |
|---|---|---|---|---|---|---|
| 40° C. | Initial | 0.50 | 100 | 0.001 | 0.2 | 0.12 |
| | 15 days | 0.50 | 100 | 0.0012 | 0.24 | 0.12 |
| | 2 months | 0.44 | 88 | 0.003 | 0.6 | 0.82 |
| | 3 months | 0.45 | 90 | 0.0083 | 1.7 | 0.3 |
| 25° C. | 3 months | 0.48 | 96 | 0.00074 | 0.15 | NIL |

As seen from the data above, epoprostenol is most stable in mannitol/arginine containing formulations when the pH of the bulk solution adjusted to 13. This is followed by arginine/trehalose formulations with the bulk solution for lyophilization adjusted to pH 13. Either trehalose or mannitol formulations with arginine at lower pH conditions are less stable at 40° C. compared to the pH 13 formulations. The simulated lyophilized Flolan formulation degraded almost completely at one month/40° C. at pH 12. At pH 13 it showed a better stability, but not as good as the mannitol/arginine/pH 13 formulation.

EXAMPLE 5

Stability of Various Reconstituted Epoprostenol Diluted to 10 µg/ml

Dilution studies were also conducted to determine whether the formulations of the present invention are suitable for IV infusion at room temperature. The stability studies were conducted at 25° C. and 30° C. to mimic the temperatures during the infusion over a 24 hour period in various large volume parenteral solutions.

To this end, the stability of the epoprostenol lyophile reconstituted and diluted to 10 µg/ml in normal saline was stability monitored for 48 hours at 25° C. and 30° C. Dilution stability of all three primary formulation batches was conducted in normal saline at 25° C. and 30° C. In addition to these studies, dilution stability studies on one lot of primary formulation batch were conducted at 25° C. and 30° C. in 5% Dextrose (D5W), WFI (in-house) and lactated Ringer's solution.

For the dilution studies, each vial was reconstituted with 5 ml of the diluent. The clear solution was transferred into a 50 ml volumetric flask. The vial was rinsed with 5 ml of diluent three times and the rinses were transferred to the flask. The contents of the flask were further diluted with the diluent and made up to the mark with the diluent. The pH of the diluted solution was measured and recorded. The contents of the flask were held at the temperatures noted and analyzed at predetermined time intervals. The dilution stability data in various diluents are presented in the Tables 19-30 below:

Dilution Studies in Normal Saline

TABLE 19

Dilution stability of Epoprostenol in Saline, Lot # EX-01 at 25° C., pH 11.58

| Assay Time | EPP (ug/ml) | % of Initial | 6-PGF* (ug/ml) | % of EPP(Initial) | Additional Peaks Area % |
|---|---|---|---|---|---|
| Initial | 10.10 | 100.0 | NIL | NIL | NIL |
| 6 hrs | 10.06 | 99.6 | NIL | NIL | NIL |
| 12 hrs | 10.02 | 99.2 | NIL | NIL | NIL |
| 18 hrs | 9.95 | 98.5 | NIL | NIL | NIL |
| 24 hrs | 9.81 | 97.1 | 0.12 | 1.19 | NIL |
| 30 hrs | 9.71 | 96.1 | 0.32 | 3.17 | NIL |
| 36 hrs | 9.62 | 95.2 | 0.40 | 3.96 | NIL |
| 42 hrs | 9.52 | 94.3 | 0.48 | 4.75 | NIL |
| 48 hrs | 9.46 | 93.7 | 0.52 | 5.14 | NIL |

*6-PGF—6-keto PGF

TABLE 20

Dilution stability of Epoprostenol in Saline, Lot # EX-01 at 30° C.

| Assay Time | EPP (ug/ml) | % of Initial | 6-PGF (ug/ml) | % of EPP(Initial) | Additional Peaks Area % |
|---|---|---|---|---|---|
| Initial | 10.10 | 100.0 | NIL | NIL | NIL |
| 6 hrs | 10.05 | 99.5 | NIL | NIL | NIL |
| 12 hrs | 9.92 | 98.2 | NIL | NIL | NIL |
| 18 hrs | 9.79 | 96.9 | 0.37 | 3.65 | NIL |
| 24 hrs | 9.62 | 95.3 | 0.59 | 5.89 | NIL |
| 30 hrs | 9.37 | 92.8 | 0.76 | 7.52 | NIL |
| 36 hrs | 9.21 | 91.2 | 0.83 | 8.22 | NIL |
| 42 hrs | 9.02 | 89.3 | 1.30 | 12.87 | NIL |
| 48 hrs | 8.94 | 88.5 | 1.34 | 13.27 | NIL |

TABLE 21

Dilution stability of Epoprostenol in Saline, Lot # EX-02 at 25° C., pH 11.58

| Assay Time | EPP (ug/ml) | % of Initial | 6-PGF (ug/ml) | % of EPP(Initial) | Additional Peaks Area % |
|---|---|---|---|---|---|
| Initial | 10.30 | 100.0 | NIL | NIL | NIL |
| 6 hrs | 10.24 | 99.4 | NIL | NIL | NIL |
| 12 hrs | 10.20 | 99.0 | NIL | NIL | NIL |
| 18 hrs | 10.00 | 97.1 | NIL | NIL | NIL |
| 24 hrs | 9.96 | 96.7 | 0.07 | 0.68 | NIL |
| 30 hrs | 9.85 | 95.6 | 0.27 | 2.62 | NIL |
| 36 hrs | 9.76 | 94.8 | 0.34 | 3.30 | NIL |
| 42 hrs | 9.68 | 94.0 | 0.44 | 4.27 | NIL |
| 48 hrs | 9.58 | 93.0 | 0.48 | 4.66 | NIL |

TABLE 22

Dilution stability of Epoprostenol in Saline, Lot # EX-02 at 30° C.

| Assay Time | EPP (ug/ml) | % of Initial | 6-PGF (ug/ml) | % of EPP(Initial) | Additional Peaks Area % |
|---|---|---|---|---|---|
| Initial | 10.20 | 100.0 | NIL | NIL | NIL |
| 6 hrs | 10.13 | 99.3 | NIL | NIL | NIL |
| 12 hrs | 10.03 | 98.3 | NIL | NIL | NIL |
| 18 hrs | 9.82 | 96.3 | 0.32 | 3.14 | NIL |
| 24 hrs | 9.70 | 95.1 | 0.52 | 5.10 | NIL |
| 30 hrs | 9.47 | 92.8 | 0.70 | 6.90 | NIL |
| 36 hrs | 9.29 | 91.1 | 0.79 | 7.74 | NIL |
| 42 hrs | 9.10 | 89.2 | 1.21 | 11.86 | NIL |
| 48 hrs | 9.02 | 88.4 | 1.27 | 12.45 | NIL |

TABLE 23

Dilution stability of Epoprostenol in Saline, Lot # EX-03 at 25° C., pH 11.6

| Assay Time | EPP (ug/ml) | % of Initial | 6-PGF (ug/ml) | % of EPP(Initial) | Additional Peaks Area % |
|---|---|---|---|---|---|
| Initial | 10.30 | 100.0 | NIL | NIL | NIL |
| 6 hrs | 10.20 | 99.0 | NIL | NIL | NIL |
| 12 hrs | 10.20 | 99.0 | NIL | NIL | NIL |
| 18 hrs | 10.00 | 97.1 | NIL | NIL | NIL |
| 24 hrs | 9.94 | 96.5 | 0.09 | 0.87 | NIL |
| 30 hrs | 9.82 | 95.3 | 0.29 | 2.81 | NIL |
| 36 hrs | 9.71 | 94.3 | 0.37 | 3.59 | NIL |
| 42 hrs | 9.61 | 93.3 | 0.46 | 4.47 | NIL |
| 48 hrs | 9.53 | 92.5 | 0.51 | 4.95 | NIL |

TABLE 24

Dilution stability of Epoprostenol in Saline, Lot # EX-03 at 30° C.

| Assay Time | EPP (ug/ml) | % of Initial | 6-PGF (ug/ml) | % of EPP(Initial) | Additional Peaks Area % |
|---|---|---|---|---|---|
| Initial | 10.20 | 100.0 | NIL | NIL | NIL |
| 6 hrs | 10.10 | 99.0 | NIL | NIL | NIL |
| 12 hrs | 9.96 | 97.6 | NIL | NIL | NIL |
| 18 hrs | 9.77 | 95.8 | 0.33 | 3.24 | NIL |
| 24 hrs | 9.61 | 94.2 | 0.58 | 5.69 | NIL |
| 30 hrs | 9.44 | 92.5 | 0.75 | 7.35 | NIL |
| 36 hrs | 9.30 | 91.2 | 0.83 | 8.14 | NIL |
| 42 hrs | 9.10 | 89.2 | 1.30 | 12.75 | NIL |
| 48 hrs | 8.96 | 87.8 | 1.33 | 13.04 | NIL |

As shown in Tables 19-24, the diluted solutions of epoprostenol were quite stable at 25° C. and 30° C. maintaining greater than 90% potency for at least a 24 hour period. All batches studied exhibited minimal batch to batch variability in stability at both temperatures. The only degradation product observed was 6-keto PGF.

Dilution Studies in D5W:

TABLE 25

Dilution stability of Epoprostenol in D5W, Lot # EX-03 at 25° C., pH 10.9

| Assay Time | EPP (ug/ml) | % of Initial | 6-PGF (ug/ml) | % of EPP(Initial) | Additional Peaks Area % |
|---|---|---|---|---|---|
| Initial | 10.20 | 100.0 | NIL | NIL | NIL |
| 2 hrs | 9.83 | 96.4 | NIL | NIL | NIL |
| 4 hrs | 9.40 | 92.2 | 0.03 | 0.29 | NIL |
| 6 hrs | 9.08 | 89.0 | 0.04 | 0.39 | NIL |
| 8 hrs | 8.81 | 86.4 | 0.07 | 0.69 | NIL |

TABLE 26

Dilution stability of Epoprostenol in D5W, Lot # EX-03 at 30° C.

| Assay Time | EPP (ug/ml) | % of Initial | 6-PGF (ug/ml) | % of EPP(Initial) | Additional Peaks Area % |
|---|---|---|---|---|---|
| Initial | 10.20 | 100.0 | NIL | NIL | NIL |
| 2 hrs | 9.76 | 95.7 | NIL | NIL | NIL |
| 4 hrs | 9.40 | 92.2 | 0.04 | 0.39 | NIL |
| 6 hrs | 9.04 | 88.6 | 0.04 | 0.39 | NIL |
| 8 hrs | 8.60 | 84.3 | 0.08 | 0.80 | NIL |

The epoprostenol degraded in 5% Dextrose solution (D5W) more than in the saline. The 6-keto PGF levels were very low, yet no other peaks were observed. Here, approximately 84% of the drug degraded after 8 hours, but no other peaks were detected as a degradation product.

The instability in D5W can be partially attributed to the significant drop in the pH, as the pH drop was more than expected. In the case of such a pH drop, D5W cannot be used for reconstitution/dilution of this present invention.

Dilution Stability Study of Epoprostenol in Water for Injection

TABLE 27

Dilution stability of Epoprostenol in WFI, Lot # EX-03 at 25° C., pH 11.55

| Assay Time | EPP (ug/ml) | % of Initial | 6-PGF (ug/ml) | % of EPP(Initial) | Additional Peaks Area % |
|---|---|---|---|---|---|
| Initial | 9.04 | 100.0 | NIL | NIL | NIL |
| 6 hrs | 8.97 | 99.2 | NIL | NIL | NIL |
| 12 hrs | 8.86 | 98.0 | NIL | NIL | NIL |
| 18 hrs | 8.77 | 97.0 | NIL | NIL | NIL |
| 24 hrs | 8.68 | 96.0 | 0.11 | 1.20 | NIL |
| 30 hrs | 8.60 | 95.1 | 0.12 | 1.30 | NIL |
| 36 hrs | 8.60 | 95.0 | 0.41 | 4.54 | NIL |
| 42 hrs | 8.43 | 93.3 | 0.46 | 5.10 | NIL |
| 48 hrs | 8.41 | 93.0 | 0.80 | 8.90 | NIL |

TABLE 28

Dilution stability of Epoprostenol in WFI, Lot # EX-03 at 30° C.

| Assay Time | EPP (ug/ml) | % of Initial | 6-PGF (ug/ml) | % of EPP(Initial) | Additional Peaks Area % |
|---|---|---|---|---|---|
| Initial | 9.04 | 100.0 | NIL | NIL | NIL |
| 6 hrs | 8.93 | 98.8 | 0.06 | 0.7 | NIL |
| 12 hrs | 8.78 | 97.1 | 0.09 | 1.04 | NIL |
| 18 hrs | 8.25 | 91.3 | 0.21 | 2.30 | NIL |
| 24 hrs | 7.27 | 80.4 | 0.48 | 5.32 | NIL |
| 30 hrs | 5.75 | 64.0 | 0.78 | 8.60 | NIL |
| 36 hrs | 3.37 | 37.3 | 1.76 | 19.5 | NIL |
| 42 hrs | 1.64 | 18.1 | 3.20 | 35.0 | 21.1 |
| 48 hrs | 0.79 | 8.73 | 4.30 | 47.2 | 26.2 |

Interestingly the stability of epoprostenol in water and normal saline at 25° C. were similar. However, epoprostenol in water degraded more rapidly at 30° C. than in normal saline. However, greater than 90% potency was maintained for more than 18 hours. Degradation accelerated after the 24 hours time point.

Dilution Stability Study in Lactated Ringer's Solution

Dilution stability in lactated Ringer's solution has also been conducted and shown in Tables 29-30 below:

TABLE 29

Dilution stability of Epoprostenol in Lactated Ringer's solution, Lot # EX-03 at 25° C., pH 11.63

| Assay Time | EPP (ug/ml) | % of Initial | 6-PGF (ug/ml) | % of EPP(Initial) | Additional Peaks Area % |
|---|---|---|---|---|---|
| Initial | 10.50 | 100.0 | NIL | NIL | NIL |
| 6 hrs | 10.43 | 99.3 | 0.17 | 1.6 | NIL |
| 12 hrs | 10.20 | 97.1 | 0.24 | 2.3 | 0.9 |
| 18 hrs | 10.08 | 96.0 | 0.25 | 2.4 | 2.0 |
| 24 hrs | 9.98 | 95.1 | 0.17 | 1.6 | 3.6 |
| 30 hrs | 9.94 | 94.7 | 0.19 | 1.8 | 3.5 |
| 36 hrs | 9.82 | 93.5 | 0.19 | 1.8 | 3.4 |
| 42 hrs | 9.74 | 92.8 | 0.18 | 1.7 | 3.2 |
| 48 hrs | 9.61 | 91.5 | 0.35 | 3.3 | 3.1 |

TABLE 30

Dilution stability of Epoprostenol in Lactated Ringer's solution, Lot # EX-03 at 30° C.

| Assay Time | EPP (ug/ml) | % of Initial | 6-PGF (ug/ml) | % of EPP(Initial) | Additional Peaks Area % |
|---|---|---|---|---|---|
| Initial | 10.50 | 100.0 | NIL | NIL | NIL |
| 6 hrs | 10.34 | 98.5 | 0.09 | 0.83 | 2.59 |
| 12 hrs | 10.31 | 98.2 | 0.13 | 1.22 | 3.85 |
| 18 hrs | 10.20 | 97.1 | 0.09 | 0.87 | 6.04 |
| 24 hrs | 9.82 | 93.5 | 0.11 | 1.00 | 6.00 |
| 30 hrs | 9.62 | 91.6 | 0.15 | 1.40 | 1.04 5.76 |
| 42 hrs | 9.26 | 88.2 | 0.18 | 1.72 | 6.24 |

The stability of epoprostenol in the lactated Ringer's solution is comparable to that of normal saline at both temperatures studied.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for making an epoprostenol composition comprising the steps of:
   (a) providing a bulk solution comprising (i) epoprostenol or a salt thereof, and (ii) an alkalinizing agent; and
   (b) adjusting the pH of the bulk solution to greater than 13.

2. The method of claim 1, further comprising the step of:
   (c) lyophilizing the adjusted bulk solution.

3. The method of claim 2, wherein step (c) comprises: freezing the adjusted bulk solution in a freezing cycle; drying the frozen solution in a primary drying cycle; and drying the frozen solution in a secondary drying cycle.

4. The method of claim 3, wherein the freezing cycle comprises:
   (i) placing the bulk solution on a shelf in a lyophilization chamber;
   (ii) cooling the shelf to less than or about −30 degrees C. at the rate of approximately 0.5 to 0.7 C./min.;
   (iii) holding the shelf at about −30 degrees C. or below for about 30 min or until the adjusted bulk solution temperature reaches less than or about −25 degrees C.;
   (iv) lowering the shelf temperature to about −45±2 degrees C. until the bulk adjusted solution temperature reaches approximately about −38±2 degrees C.;
   (v) holding the bulk solution at about −38±2 degrees C. for about six hours or more;
   (vi) applying vacuum until the lyophilization chamber pressure reaches about 50 milliTorr or less; and
   (vii) maintaining the shelf temperature at about −45±2 degrees C. for about 45 minutes or more after vacuum application.

5. The method of claim 4, wherein the primary drying cycle comprises the steps of:
   (i) raising the shelf temperature to about 0±2 degrees C. at the heating rate of about 20±2 degrees C. per hour and continue drying under vacuum until the product temperature reaches about −3±2 degrees C. or higher; and
   (ii) raising the shelf temperature to about 25±2 degrees C. and continue drying until the product temperature reaches about 20 degrees C. or higher.

6. The method of claim 4, wherein the secondary drying cycle comprises the steps of:
  (i) raising the shelf temperature to about 45±2 degrees C. at a rate of about 3 ±2 degrees C./hr and continue drying until the product temperature reaches about 38±2 degrees C. or higher;
  (ii) turning off the vacuum while increasing the chamber pressure with nitrogen; and
  (iii) when the chamber pressure reaches atmospheric pressure, discontinuing the nitrogen and enclosing the composition under a nitrogen atmosphere.

7. The method of claim 1, wherein the ratio of epoprostenol or a salt thereof to alkalinizing agent is about 1:25 to about 1:200.

8. The method of claim 1, wherein the alkalinizing agent is selected from the group consisting of arginine, lysine, meglumine, N-methyl glucosomine, an amino acid with a pKa of 9.0 and above, trisodium phosphates, sodium carbonates, and tetrasodium-EDTA.

9. The method of claim 1, wherein the bulk solution further comprises (iii) a bulking agent.

10. The method in claim 9, wherein the bulking agent is selected from the group consisting of hydroxyl ethyl starch (HES), sorbitol, lactose, dextran, maltose, mannose, ribose, sucrose, mannitol, trehalose, lactose, dextran, cyclodextrin, glycine, and polyvinylpyrrolidine (PVP).

11. The method of claim 9, wherein the bulking agent is present at about 1-10%.

12. The method of claim 1, wherein the epoprostenol salt is epoprostenol sodium.

13. The method of claim 1, wherein step (b) comprises adding an organic or inorganic base.

14. The method of claim 13, wherein the inorganic base is selected from the group consisting of sodium hydroxide, potassium hydroxide, magnesium hydroxide, and ammonium hydroxide.

15. The method of claim 13, where the organic base is selected from the group consisting of aromatic amines and aromatic alcohols.

16. A method for treating a patient suffering from a disease selected from the group consisting of cardiovascular disease, atherosclerosis, arteriosclerosis, congestive heart failure, angina pectoris, and hypertension, said method comprising the steps of (1) combining an intravenous fluid with an effective amount of a lyophilized pharmaceutical composition comprising:
  (a) a unit dose of 0.5 mg or 1.5 mg of epoprostenol or a salt thereof;
  (b) arginine; and
  (c) sodium hydroxide,
wherein said lyophilized pharmaceutical composition is formed from a bulk solution having a pH of 13 or higher; and (2) administering the resulting intravenous fluid of step (1) to a patient in need thereof.

17. The method of claim 16, wherein step (1) comprises the step of reconstituting the lyophilized pharmaceutical composition with a first diluent prior to the administrating step to form a reconstituted solution.

18. The method of claim 17, wherein the first diluent is one of water for injection, 0.9% sodium chloride solution, lactated Ringer's solution, Ringer's solution, sodium carbonate solution, or bicarbonate solution.

19. The method of claim 17, wherein step (1) further comprises the step of diluting the reconstituted solution with a second diluent to form a diluted solution.

20. The method of claim 19, wherein the diluted solution is hemocompatible.

21. The method of claim 17, wherein the reconstituted solution is self-preserved.

22. A method for treating a patient suffering from a disease selected from the group consisting of cardiovascular disease or disorder, atherosclerosis, arteriosclerosis, congestive heart failure, angina pectoris, and hypertension, said method comprising the steps of (1) combining an intravenous fluid with an effective amount of a lyophilized pharmaceutical composition comprising:
  (a) a unit dose of 0.5 mg or 1.5 mg of epoprostenol or a salt thereof;
  (b) 50 mg of arginine;
  (c) Mannitol or sucrose; and
  (d) sodium hydroxide.
wherein said lyophilized pharmaceutical composition is formed from a bulk solution having a pH of 13 or higher; and (2) and (2) administering the resulting intravenous fluid of step (1) to a patient in need thereof.

23. The method of claim 22, wherein step (1) comprises the step of reconstituting the lyophilized pharmaceutical composition with a first diluent prior to the administrating step to form a reconstituted solution.

24. The method of claim 23, wherein the first diluent is one of water for injection, 0.9% sodium chloride solution, lactated Ringer's solution, Ringer's solution, sodium carbonate solution, or bicarbonate solution.

25. The method of claim 23, wherein step (1) further comprises the step of diluting the reconstituted solution with a second diluent to form a diluted solution.

26. The method of claim 25, wherein the diluted solution is hemocompatible.

27. The method of claim 23, wherein the reconstituted solution is self-preserved.

28. The method of claim 22, wherein the intravenous fluid of step (1) is water for injection.

29. The method of claim 22, wherein the intravenous fluid of step (1) is 0.9% sodium chloride solution.

30. The method of claim 22, wherein the intravenous fluid of step (1) is 5 mL of water for injection or 0.9% sodium chloride solution.

31. The method of claim 22, wherein the administration step (2) comprises administration by injection or infusion.

32. A method for treating a patient suffering from a disease selected from the group consisting of cardiovascular disease, atherosclerosis, arteriosclerosis, congestive heart failure, angina pectoris, and hypertension, said method comprising the steps of (1)(i) reconstituting an effective amount of a lyophilized pharmaceutical composition comprising:
  (a) a unit dose of 0.5 mg or 1.5 mg of epoprostenol or a salt thereof;
  (b) 50 mg of arginine;
  (c) Mannitol or sucrose; and
  (d) sodium hydroxide,
in 5 mL of water for injection or 0.9% sodium chloride solution to form a reconstituted solution, wherein said lyophilized pharmaceutical composition is formed from a bulk solution having a pH of 13 or higher; (1)(ii) diluting the reconstituted solution of step (1)(i) with a second diluent to form a diluted solution; and (2) administering the resulting diluted solution of step (1)(ii) to a patient in need thereof.

33. The method of claim 32, wherein the epoprostenol or a salt thereof is epoprostenol sodium.

34. The method of claim 33, wherein the second diluent in step (1)(ii) is the same diluent as the first diluent used in step (1)(i) to reconstitute the lyophilized composition.

35. The method of claim 33, wherein the administration step (2) comprises administration by injection or infusion.

36. The method of claim 16, wherein the intravenous fluid of step (1) is water for injection.

37. The method of claim 16, wherein the intravenous fluid of step (1) is 0.9% sodium chloride solution.

38. The method of claim 16, wherein the intravenous fluid of step (1) is 5 mL of water for injection or 0.9% sodium chloride solution.

39. The method of claim 16, wherein the administration step (2) comprises administration by injection or infusion.

40. A method for treating a patient suffering from a disease selected from the group consisting of cardiovascular disease, atherosclerosis, arteriosclerosis, congestive heart failure, angina pectoris, and hypertension, said method comprising the steps of (1)(i) reconstituting an effective amount of a lyophilized pharmaceutical composition comprising:

(a) a unit dose of 0.5 mg or 1.5 mg of epoprostenol or a salt thereof;
  (b) 50 mg of arginine;
  (c) Mannitol or sucrose; and
  (d) sodium hydroxide, in 5 mL of water for injection to form a reconstituted solution, wherein said lyophilized pharmaceutical composition is formed from a bulk solution having a pH of 13 or higher; (1)(ii) diluting the reconstituted solution of step (1)(i) with water for injection to form a diluted solution; and (2) administering the resulting diluted solution of step (1)(ii) to a patient in need thereof.

41. The method of claim 40, wherein the epoprostenol or a salt thereof is epoprostenol sodium.

42. The method of claim 41, wherein the administration step (2) comprises administration by injection or infusion.

* * * * *

UNITED STATES PATENT AND TRADEMARK OFFICE
CERTIFICATE OF CORRECTION

PATENT NO. : 8,598,227 B2  
APPLICATION NO. : 13/621489  
DATED : December 3, 2013  
INVENTOR(S) : Nagesh R. Palepu Page 1 of 1

It is certified that error appears in the above-identified patent and that said Letters Patent is hereby corrected as shown below:

On the Title Page: Item (73)  
Please replace the Assignee "Actelion Pharmaceuticals Ltd., Allschwil (CH)" that appears on the title page of the patent with "Actelion One SA, Luxembourg (LU)".

In the Claims:  
Please delete "and (2)" in column 20, claim 22, line 17 of the patent.

Signed and Sealed this  
Sixth Day of May, 2014

Michelle K. Lee  
*Deputy Director of the United States Patent and Trademark Office*